United States Patent [19]

Sheng et al.

[11] Patent Number: 4,640,130
[45] Date of Patent: Feb. 3, 1987

[54] METHOD AND APPARATUS FOR ACOUSTICALLY MEASURING THE VOLUME OF AN OBJECT

[75] Inventors: Hwai-Ping Sheng, Bellaire; Cutberto Garza, Houston; Dean C. Winter, Houston; William G. Deskins, Houston, all of Tex.

[73] Assignee: Baylor College of Medicine, Houston, Tex.

[21] Appl. No.: 665,800

[22] Filed: Oct. 29, 1984

[51] Int. Cl.[4] .................... G01N 29/00; G01F 17/00
[52] U.S. Cl. ........................................ 73/579; 73/149
[58] Field of Search .................................. 73/579, 149

[56] References Cited

U.S. PATENT DOCUMENTS 3,237,451  3/1966  Haeff .................................. 73/149
4,072,046  2/1978  Lao .................................... 73/149
4,535,627  8/1985  Prost et al. ......................... 73/149

FOREIGN PATENT DOCUMENTS 1009002 11/1965 United Kingdom ................. 73/571

972230 11/1982 U.S.S.R. .............................. 73/149

Primary Examiner—Howard A. Birmiel
Attorney, Agent, or Firm—Fulbright & Jaworski

[57] ABSTRACT

A non-invasive method and apparatus for measuring the volume of an object such as an infant using the principle of the Helmholtz resonator. A container having a cavity therein containing gas and having an opening is subjected to a variable frequency loud speaker. The resonance frequency of the cavity is proportional to the volume of the cavity. By placing an object to be measured in the cavity, the change in the resonance frequency of the cavity before and after the object is placed is an indication of the volume of the object. The loudspeaker is mechanically uncoupled from the opening, the volume of the cavity is large enough compared to the object to be measured so the object will not change the shape of the cavity, and the temperature inside the cavity is maintained substantially constant during the measurements. Various lung measurements may be taken by determining the volume of air inhaled or exhaled from the lungs of an animal.

8 Claims, 5 Drawing Figures

METHOD AND APPARATUS FOR ACOUSTICALLY MEASURING THE VOLUME OF AN OBJECT

BACKGROUND OF THE INVENTION

The most widely used techniques for measuring the volume of a human body are underwater or hydrostatic weighing and water displacement. However, since both techniques involve subject submersion, they are both inappropriate for use with infants and newborns.

The present invention is directed to a noninvasive apparatus and method to measure volume of an object, such as infants, using the principle of the Helmholtz Resonator. The Helmholtz Resonator consists of a container having a cavity having an enclosed volume of gas which can be caused to resonate acoustically through an opening in the container by the imposition of periodic pressure fluctuations at the opening. The classic equation for the resonance frequency for the Helmholtz Resonator is $$(c/2\pi) \left[ \frac{A}{V(l + \frac{1}{2}\pi R)} \right]^{\frac{1}{2}}$$

Where c is the speed of sound in the gas, A is the cross-sectional area of the opening, V is the volume of the resonating cavity, l is the length of the neck of the opening and R is the radius of the opening. From this equation, it is seen that the resonance frequency is inversely proportional to the square root of the cavity volume. If the volume of the resonating cavity changes, the resonance frequency will also change. The present invention uses this basic characteristic of the Helmholtz Resonator by measuring the resonance frequency of the cavity in the container before and after an object, such as an infant, is placed inside of the cavity. The difference in the two resonance frequencies can then be calibrated in terms of the total object volume.

SUMMARY OF THE INVENTION

The present invention is directed to a method and apparatus for accoustically measuring the volume of an object by determining the resonance frequency of a cavity in a container, and measuring the change in the resonance frequency of the cavity before and after an object is placed inside of the cavity whereby comparison of the two measurements is an indication of the volume of the object.

An object of the present invention is the provision of an apparatus for measuring the volume of an object by providing a container adapted to receive the object to be measured and having gas therein in which the container has an opening. Variable frequency means are provided for producing period pressure fluctuations at the mouth of the opening and means are provided for measuring the resonance frequency in the container.

Still a further object of the present invention is wherein the pressure fluctuation producing means is acoustically complete but mechanically uncoupled from the opening so that a uniform and normal pressure wave front impinges on the opening.

Still a further object of the present invention is wherein the container includes a cavity which is large enough compared to the volume of the object to be measured whereby the object will not significantly change the shape of the cavity.

A further object of the present invention includes means for keeping the temperature inside of the container substantially constant during the measurement to avoid changes in temperature which adversely affect the measurements.

A still further object of the present invention is wherein the container has a cavity which is at least eight times larger than the object whose volume is to be measured so that the addition of the object does not substantially change the shape of the cavity.

Still a further object of the present invention is wherein the resonance frequency measurement includes sound monitoring means which is filtered in order to minimize interference from extraneous noise in the environment.

Still a further object is wherein the pressure fluctuation producing means, such as a loudspeaker, is separated from the container opening a distance sufficient to avoid accoustical reflections between the container and the loudspeaker.

Yet a further object of the present invention is the provision of an apparatus for measuring the volume of an object including a symmetrical container having a cavity therein containing gas in which the container has a single opening. The container has an openable and closable portion for inserting the object to be measured into the cavity and the volume of the cavity is large enough compared to the volume of the object to be measured whereby the object will not significantly change the shape of the cavity. A variable frequency sound-producing loudspeaker is positioned to direct sound waves into the opening but the loudspeaker is mechanically uncoupled from the opening. Means are provided for measuring the resonance frequency of the cavity.

Still a further object of the present invention is wherein feedback means is provided between the frequency measuring means and the loudspeaker for operating the loudspeaker at the resonance frequency of the cavity for more easily measuring changes that occur in the object to be measured, such as an infant, for providing a measurement of various lung volumes.

Yet a further object of the present invention is the method of determining the volume of air inhaled or exhaled from the lungs of an animal, such as an infant, by placing the infant into a cavity of a container having an opening to which is applied sound wave pressure fluctuations. The frequency of the pressure fluctuations is changed to provide a resonance frequency in the gas and the cavity as the volume of air in the lungs of the infant changes. The measurement consists of measuring the resonance frequencies as the volume of air in the lungs change and comparing the differences in the measured resonance frequencies which is an indication of volume changes in the lung. One measurement that can be performed is measuring the tidal volume of the lungs.

Other and further objects, features and advantages will be apparent from the following description of a presently preferred embodiment of the invention, given for the purpose of disclosure and taken in conjunction with the accompanying drawings.

DESCRIPTION OF THE PREFERRED EMBODIMENT

While the present invention is particularly useful for measuring a body volume of humans and specifically infants, and will be generally described in connection with that particular application, for purposes of illustration only, the present invention is also useful for measuring the volume of various other objects such as inanimate objects.

Figure 1:
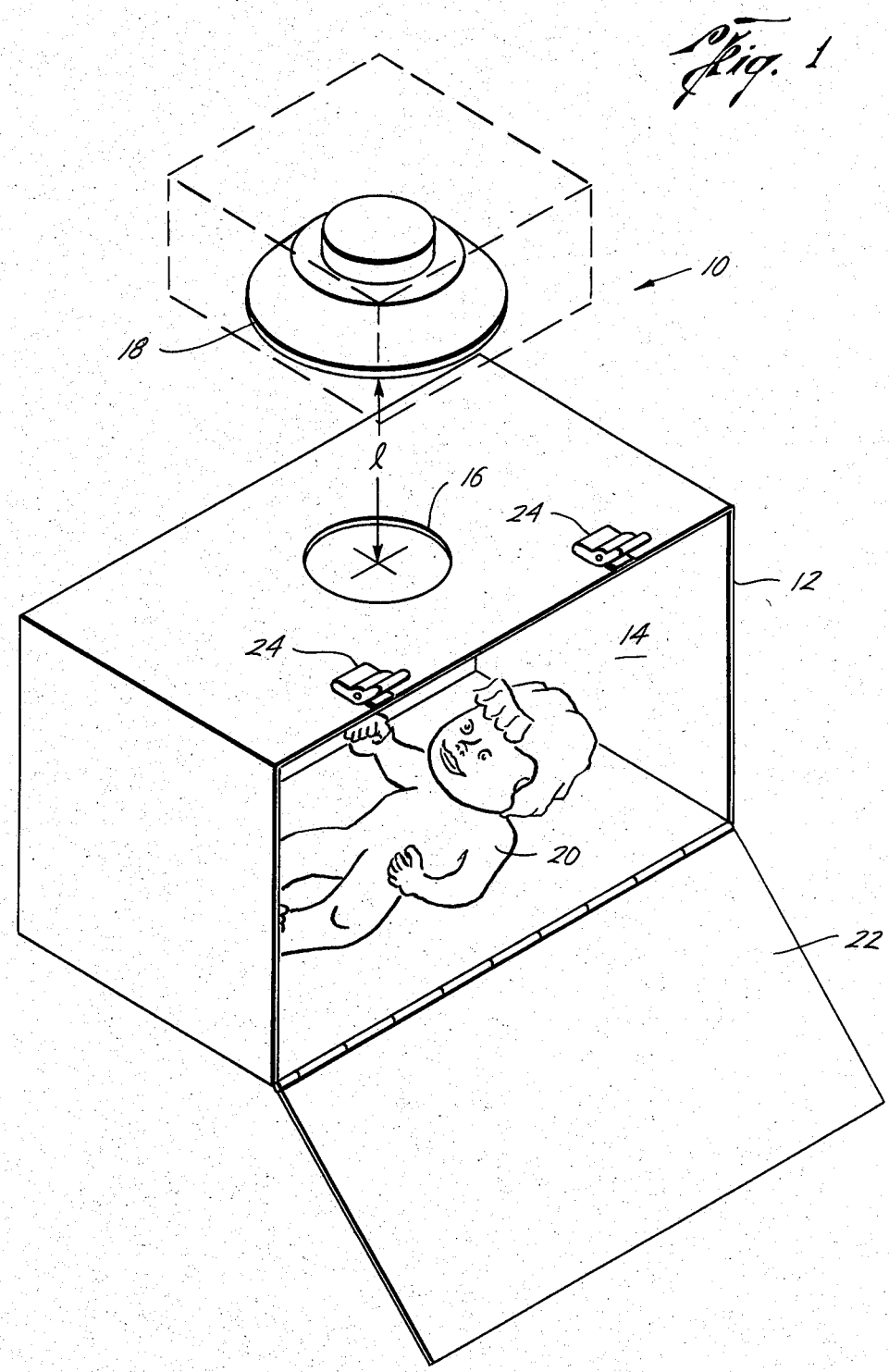
FIG. 1 is a perspective view of the preferred embodiment of the present invention.

Referring now to FIG. 1, the present invention is generally indicated by the reference numeral 10 and includes a container 12 having a cavity 14 therein containing gas, such as air, which is exposed to the outside of the container 12 through an opening 16. Variable frequency means for producing periodic pressure fluctuations, such as a loudspeaker 18, is provided for directing the pressure fluctuation through the opening 16 whereby the gas in the cavity 14 can be caused to resonate acoustically in accordance with the formula given above wherein A is the crosssectional area of the opening 16, V is the volume of the cavity 14, l is the length of the neck of the opening as shown in FIG. 1, and R is the radius of the opening 16.

As previously discussed, the resonance frequency of the cavity 14 corresponds directly to the volume of the space of the cavity 14. Therefore, a change in the resonance frequency of the cavity before and after an object, such as an infant 20, is placed in the cavity 14 can be used to measure the body volume of the infant 20.

However, in order to obtain the desired accuracy, various other factors were considered. For best results, the shape and size of the cavity 14 are important. In order to minimize shape changes when the infant 20 is added to the cavity 14, the shape of the cavity should be simple and symmetric and the volume of the cavity 14 should be large enough so that the introduction of the infant 20 does not significantly or radically alter the shape of the cavity. In the embodiment tested, a rectangular container 12 having inside dimensions of 20×20×45 cm was provided of acrylic in which the wall thickness was 1.27 cm. The container 12 included an openable and closable portion such as a hinged front lid 22 having closed cell thereon to provide an acoustical seal when the lid 22 was locked into place by the latches 24. The cavity 14 had a volume of 18 liters which was large enough to hold the range of newborn infants for which the system was initially designed. The ratio of the infant's body volume to the cavity volume was less than 10% which minimized any shape changes that would occur when the infant 20 was placed inside the cavity 14. Preferably, the volume of the cavity 14 should be as least eight times larger than the volume of the object 20 to be measured.

Figure 2:
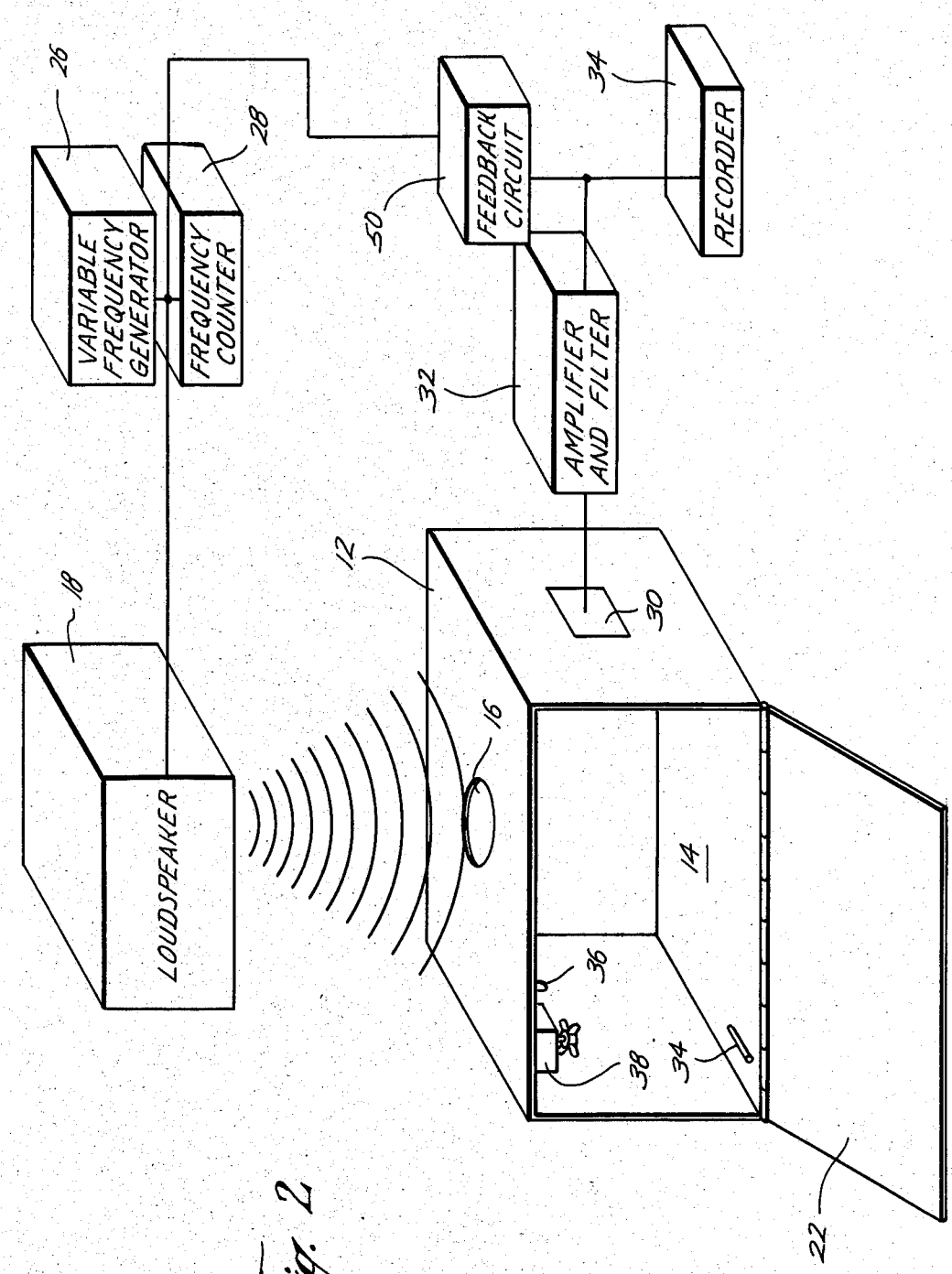
FIG. 2 is a perspective embodiment of the preferred invention with the associated controls.

In an early embodiment the loudspeaker 18 was enclosed in a housing which extended to the container 12 for minimizing external acoustical interference. However, such a system was not satisfactory. The quality factor in the system was dramatically increased by mechanically uncoupling the loudspeaker 18 from the cavity 14 and suspending the loudspeaker 18 above the opening 16, as shown in FIGS. 1 and 2, so that a uniform and normal pressure wave front from the loudspeaker 18 impinged on the opening 16. Since the loudspeaker 18 no longer mechanically loaded the cavity 14, the considerable viscous losses in the suspension of the loudspeaker 18 was not added to those of the cavity 14. A uniform pressure wave impinging on the cavity opening 16 was maintained as long as the opening 16 was not in the near field of the loudspeaker 18. For a 20 cm loudspeaker operating at frequencies near 100 HZ, the near field is effectively absent. However, initial testing of the system shows that if the resonating cavity 14 and loudspeaker 18 were too close to one another, the resonance frequency shifted. This was apparently due to the influence of reflections between the two surfaces as they were brought closer together. At separations greater than 70 cm, the influence of reflections ceased to be a factor.

The original Helmholtz theory established the criteria that the resonance frequency wavelength should be sixteen times the largest cavity dimension. Since the largest dimension of the actual container 12 selected was 30 cm, the distance from the opening 16 to one corner of the cavity 14, the resonance frequency is calculated to be 72 HZ. Therefore, frequencies of 72 HZ or less will satisfy the long wavelength assumption. However, for several reasons it is desirable to have as high as resonance frequency as possible. First, loudspeakers and microphones that respond well at very low frequencies tend to be expensive. Secondly, human hearing response decreased significantly at low frequency and it is desirable for safety reasons that the technician operating the system hear the excitation tone. Thirdly, at low frequencies interference from environmental noises such as air conditioning systems is nearly inescapable. Fourthly, frequencies near 60 HZ should be avoided because of the frequency of the supply voltage. More importantly, however, the higher the resonance frequency, the greater the absolute shift in resonance when the object 20 is placed in the cavity 14 and therefore, the greater the resolution of the system. For these reasons, a preferred resonance frequency close to 100 HZ was chosen. This gave a wavelength to largest dimension ratio of 12, which was satisfactory. Therefore, the length l and diameter of the opening 16 were selected to determine the desired resonance frequency. In tests, the quality factor decreased substantially for effective diameters of less than 8 cm for the opening 16. However, a diameter of 7.5 cm was chosen to take advantage of the higher quality factor while maintaining as high as possible the ratio of resonance wavelength to largest dimension.

Figure 3:
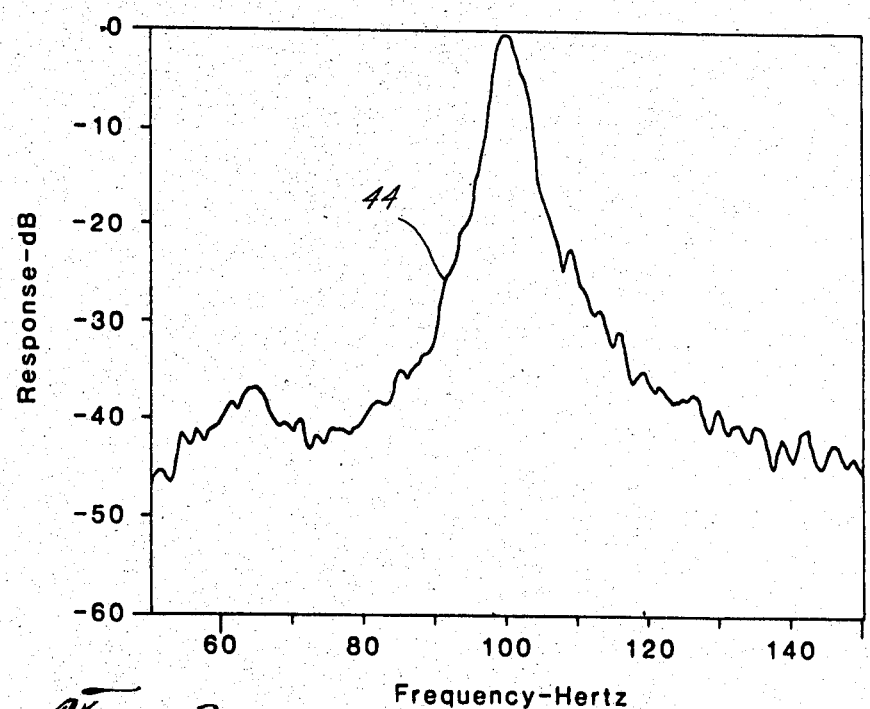
FIG. 3 is a graph illustrating the measurement of resonance frequency with a sound monitor such as a microphone.

Referring now to FIG. 2, the loudspeaker, such as Altec Model 409-HD was driven by a variable frequency generator 26 such as a sine wave generator such as Wavetek Model 188 which was modified to include a vernier frequency control and was monitored by a frequency counter 28. In order to measure the resonance frequency in the cavity 14, the sound pressure level in the cavity 14 was monitored using a condenser-type microphone 30 mounted on the side of the container 12 such as Crown Model PZM-6S powered by Crown PX-18 transformer/power supply. As best seen in FIG. 3, the frequency response graph 44 of the loudspeaker 18 and microphone 30 was excellent over the operating range so that the microphone could determine the resonance frequency by referring to the frequency counter 28. However, the cavity 14 was responsive not only to the loudspeaker 18 in the uncoupled system of FIGS. 1 and 2, but was also responsive to any other sound source in the surroundings. In order to minimize interference from sound other than near the driving frequency, the output of the microphone 30 passed through an amplifier and filter 32 which included an eighth order Butterworth active band pass filter tuned to a frequency band between 100 and 110 HZ. Any suitable recorder 34 such an oscilloscope may be used to monitor the signal.

However, the effects of temperature are significant due to the dependence of the speed of sound on the ambient temperature of the gas in the cavity 14. For example, a change in temperature of 0.1° C. results in a shift of the resonance frequency of nearly 0.02 HZ. In addition, the body heat systems of premature infants requires that the infant be kept at 35° C. Therefore, in measuring the volume of infants, space heaters are used to control the ambient temperature at the desired level by thermometers 34 and 36 mounted near the bottom and top, respective of the cavity 14. In addition, a fan 38 is provided to circulate the air and keep it uniform. The fan 38 was turned off when actual measurements were taken.

Figure 4:
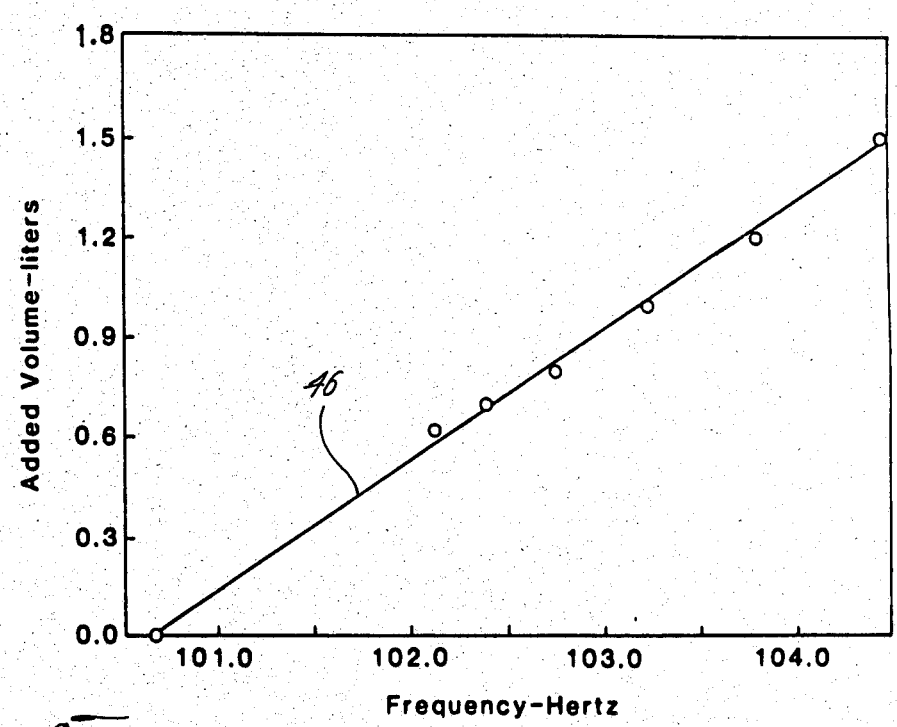
FIG. 4 is a graph illustrating the change in resonance frequency at 21.5° C. relative to the volume of an object measured.

In operation, after temperature control and electronic systems have stabilized, the resonance frequency of the apparatus 10 is measured without the object to be measured inside of the cavity 14. The loudspeaker 18 output is adjusted so that, at resonance, the sound pressure level inside the cavity 14 does not exceed 80 dB. This is to insure that an infant 20 in the cavity is not subjected to excessive levels of noise. Next, the object 20 to be measured is placed inside of the cavity 14 through the lid 22 and the procedure is performed again for the unknown volume. The difference in the resultant resonance frequencies can be converted to the corresponding volume by appropriate calibration. Referring now to FIG. 4, a graph 46 is shown showing the volume of the measured object relative to the resonance frequency of the apparatus 10. Results of actual tests for inanimate objects agree within two percent with comparable measurements by dimensional analysis and water displacement. Results of animal body volume measurement compare favorably, (within five percent) with those obtained by using a techniques of hydrostatic weighing and water displacement.

Figure 5:
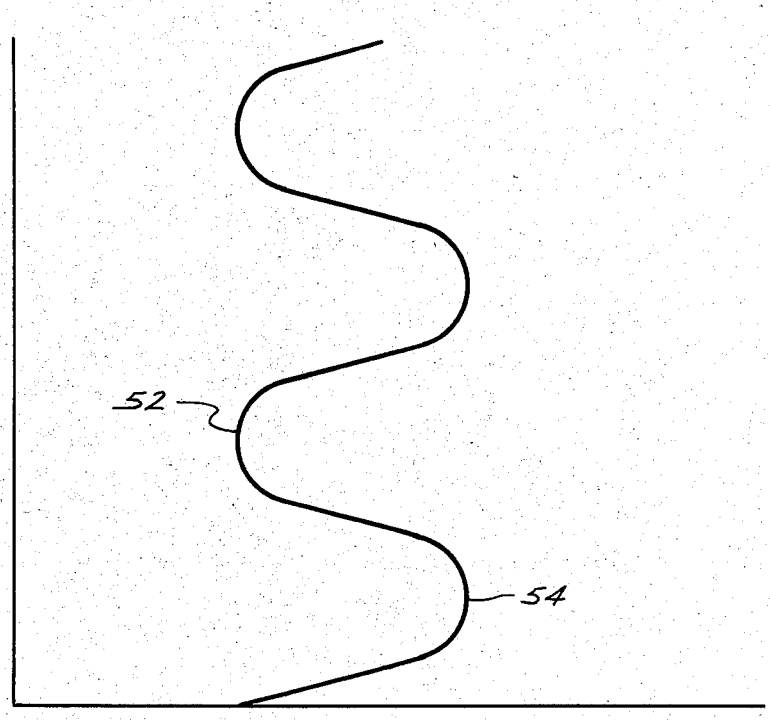
FIG. 5 is a graph illustrating the change in resonance frequency as the lungs of an animal, such as a human, change during breathing.

Movement of the infant 20 is somewhat detrimental to the measurement procedure. That is, resonance frequency will change during normal breathing and therefore requires additional time to average out the fluctuations caused by the movement of the chest wall. However, the movement of the chest wall provides the opportunity for measuring various lung parameters except for the respiratory dead space in the lungs. For example, referring to FIG. 2 a feedback circuit 50 is provided for continually maintaining resonance in the cavity 14 as the volume, such as the volume of air in a person's lung changes. Therefore, the change in the breathing volume can be measured. For example, referring to FIG. 5, it is noted that the resonance frequency changes as the lungs expand and contract with time. Therefore, with proper correlation, the difference between the resonance frequency 52 and 54 is a measurement of the tidal volume of a person or animal during breathing. Other suitable lung volume measurements can also be similarly performed.

While the method of determining the volume of an object is apparent from the description of the foregoing apparatus, the method comprehends measuring the resonance frequency of the cavity having a gas therein, when empty, of a container having an opening to which pressure fluctuations is applied, placing the object to be measured in the cavity, and again measuring the resonance frequency of the gas in the cavity with the object in the cavity. By comparing the differences between the first and second measurements an indication of the volume of the object is attained. The method further comprehends making the measurements while maintaining the temperature inside the container substantially constant during the first and second measurements. The method further comprehends measuring the volume of an animal such as a human. The method provides that the volume of the cavity is large enough relative to the volume of the object being measured so that the object will not significantly change the shape of the cavity when the object is placed in the cavity. The method further comprehends determining the volume of air inhaled or exhaled from the lung of an animal by placing the animal into a cavity of a container having an opening to which is applied sound waves pressure fluctuations, changing the frequency of the pressure fluctuations to provide resonance frequency in the cavity as the volume of air in the lungs of the animal changes, and measuring the resonance frequency as the volume of air in the lungs change, and comparing the differences in the measured resonance frequencies which is an indication of the volume changes in the lungs.

The present invention, therefore, is well adapted to carry out the objects and attain the ends and advantages as well as others inherent therein. While a presently preferred embodiment of the invention has been given for the purpose of disclosure, numerous changes in details of construction and arrangement of parts and steps of the method may be made without departing from the spirit of the invention and the scope of the appended claims.

What is claimed is:

1. An apparatus for measuring the volume of an object comprising:
    a container adapted to receive the object to be measured and having gas therein, said container having an opening;
    variable frequency means positioned for producing periodic pressure fluctuations at the mouth of the opening;
    means for measuring the resonance frequency in the container; and
    wherein said pressure fluctuation producing means is mechanically uncoupled from the opening so that a uniform and normal pressure wavefront impinges on the opening.

2. An apparatus for measuring the volume of an object comprising:
    a container adapted to receive the object to be measured and having gas therein, said container having an opening;
    variable frequency means positioned for producing periodic pressure fluctuations at the mouth of the opening;
    means for measuring the resonance frequency in the container; and wherein said pressure fluctuation producing means is separated from the opening a distance sufficient to avoid acoustical reflections between the container and the pressure fluctuation producing means.

3. An apparatus for measuring the volume of an object comprising,
   a container having a cavity therein containing gas, said container having a single opening, said container being substantially symmetrical and having an openable and closable portion for inserting the object to be measured into the cavity,
   the volume of said cavity being large enough compared to the volume of the object to be measured whereby the object will not significantly change the shape of the cavity,
   a variable frequency sound producing loudspeaker positioned to direct sound waves into the opening, but the loudspeaker is mechanically uncoupled from the opening, and
   means for measuring the resonance frequency in the cavity.

4. The apparatus of claim 3 wherein the volume of the cavity is at least eight times the volume of the object to be measured.

5. The apparatus of claim 3 including,
   feedback means between the resonance frequency measuring means and the loudspeaker for operating the loudspeaker at the resonance 6. A method of determining the volume of air inhaled or exhaled from the lungs of an animal comprising,
   placing the animal into a cavity of a container having an opening to which is applied sound waves pressure fluctuations,
   changing the frequency of the pressure fluctuations to provide resonance frequency in the cavity as the volume of air in the lungs of the animal changes; and
   measuring the resonance frequencies as the volume of air in the lungs changes; and
   comparing the difference in the measured resonance frequencies which is an indication of the volume changes in the lungs.

7. The method of claim 6 wherein the tidal volume of the lungs are measured.

8. A method for determining the volume of an animal comprising,
   measuring the resonant frequency of the cavity having a gas therein, when empty, of a container having an opening to which is applied pressure fluctuations, the cavity having at least eight times larger volumes than the animal to be measured, the pressure fluctuations being produced by means which are mechanically spaced from the opening so that a uniform and normal pressure wavefront impinges on the opening,
   placing the animal to be measured into the cavity, and again measuring the resonant frequency of the gas in the cavity with the animal in the cavity, and
   comparing the difference between the first and second measurements which is an indication of the volume of the animal.

* * * * *